United States Patent [19]

Lechtken et al.

[11] 4,292,152

[45] Sep. 29, 1981

[54] PHOTOPOLYMERIZABLE RECORDING COMPOSITION CONTAINING ACYLPHOSPHINE OXIDE PHOTOINITIATOR

[75] Inventors: Peter Lechtken; Bernd Bronstert, both of Frankenthal; Gerhard Hoffmann, Otterstadt; Rudolf Vyvial; John Lynch, both of Ludwigshafen, all of Fed. Rep. of Germany

[73] Assignee: BASF Aktiengesellschaft, Fed. Rep. of Germany

[21] Appl. No.: 55,361

[22] Filed: Jul. 6, 1979

[30] Foreign Application Priority Data

Mar. 14, 1979 [DE] Fed. Rep. of Germany ....... 2909992

[51] Int. Cl.$^3$ .............................................. C08F 2/48
[52] U.S. Cl. ............................ 204/159.15; 101/395; 204/159.23; 430/627; 525/59; 525/421; 525/445
[58] Field of Search ...................... 204/159.15, 159.23

[56] References Cited

U.S. PATENT DOCUMENTS

| | | | |
|---|---|---|---|
| 3,551,148 | 12/1970 | Faulhaber et al. | 96/35.1 |
| 3,682,808 | 8/1972 | Krauch et al. | 204/159.15 |
| 3,695,877 | 10/1972 | Taneda et al. | 96/35.1 |
| 3,715,293 | 2/1973 | Sandner et al. | 204/159.14 |
| 3,759,807 | 9/1973 | Osborn et al. | 204/159.23 |
| 3,801,329 | 4/1974 | Sandner et al. | 96/115 P |
| 3,832,188 | 8/1974 | Bamba et al. | 204/159.15 |
| 3,845,162 | 10/1974 | Hess et al. | 204/159.15 |

*Primary Examiner*—Harold D. Anderson
*Attorney, Agent, or Firm*—Keil & Witherspoon

[57] ABSTRACT

A photopolymerizable recording composition which comprises a mixture, containing a photoinitiator, of (a) a photopolymerizable olefinically unsaturated monomer and (b) an organic polymeric binder, wherein the photoinitiator is an acylphosphine oxide compound of the formula $R^1R^2PO-CO-R^3$, where $R^1$ and $R^2$ are certain organic radicals and $R^3$ is tert.-alkyl or a cyclic radical with two substituents in the ortho-position to the carbonyl group. The recording compositions have a high reactivity when irradiated with UV light and are used in particular for the preparation of printing plates, relief plates and photoresists.

6 Claims, No Drawings

PHOTOPOLYMERIZABLE RECORDING COMPOSITION CONTAINING ACYLPHOSPHINE OXIDE PHOTOINITIATOR

The present invention relates to improved photopolymerizable recording compositions which consist mainly of a mixture, containing a photoinitiator, of (a) one or more monomers having one or more photopolymerizable olefinically unsaturated double bonds, and (b) one or more organic polymeric binders, wherein the photoinitiator is an acylphosphine oxide compound.

Photopolymerizable recording compositions, as used for the preparation of printing plates and relief plates, have been frequently described and include both liquid and solid forms. For example, such recording compositions are described in German Laid-Open Application DOS No. 2,040,390 and French Pat. No. 1,520,856. The photoinitiators used for the recording compositions are in the main aromatic ketones, eg. benzil ketals, benzoin ethers and α-methylol derivatives of benzoin ethers. Though these initiator systems given useful results, modern methods of recording, in particular newspaper printing, increasingly call for shorter exposure times, a demand which cannot be met satisfactorily by using the conventional photoinitiator systems. Thus, the conventional water-washable printing plates are so slow to react that sufficient sensitization must be ensured by resorting to the artifice of pre-exposure. However, apart from other disadvantages, this entails an additional operation.

Using the recording compositions containing conventional initiator systems, the development of the relief image is also frequently not good, and must be improved by special measures, for example by adding photochromic compounds, controlling the light reflection from the metal support, or adding special inhibitors which, however, lengthen the required exposure time.

It is an object of the present invention to provide more rapid, more reactive initiators which improve the light sensitivity of recording compositions whilst, where possible, also improving the relief image.

We have found that this object is achieved, surprisingly, with certain acylphosphine oxide compounds which permit substantially more rapid curing of photopolymeric recording systems than is possible with conventional photoinitiators, and which are also capable of improving the relief image of photopolymer relief plates.

Accordingly, the present invention relates to photopolymerizable recording materials, especially for the preparation of printing plates and relief plates, which consist mainly of a mixture, containing a photoinitiator, of (a) one or more monomers possessing one or more photopolymerizable olefinically unsaturated double bonds, and
(b) one or more organic polymeric binders, wherein the photoinitiator is an acylphosphine oxide compound of the formula

where $R^1$ is alkyl of 1 to 6 carbon atoms, cycloalkyl of 5 or 6 ring carbon atoms, aryl which is unsubstituted or substituted by halogen, alkyl or alkoxy, or a S-containing or N-containing five-membered or six-membered heterocyclic radical, $R^2$ has one of the meanings of $R^1$, but $R^1$ and $R^2$ may be identical or different, or is alkoxy, aryloxy or aralkoxy, or $R^1$ and $R^2$ together form a ring, and $R^3$ is tertiary alkyl of 4 to 18 carbon atoms or tertiary cycloalkyl of 5 or 6 ring carbon atoms or is a cycloalkyl, aryl or 5-membered or 6-membered heterocyclic radical which contains substituents A and B at least in the two positions ortho to the carbonyl group, A and B being identical or different and each being alkyl, alkoxy, alkoxyalkyl, alkylthio, cycloalkyl, aryl or halogen.

The phrase "which contains substituents A and B in the two positions ortho to the carbonyl group" means that the substituents A and B are bonded to the two ring carbon atoms, capable of substitution, which are adjacent to the point of attachment of the carbonyl group. This means that the α-naphthyl radical contains the substituents A and B at least in the 2- and 8-positions and the β-naphthyl radical at least in the 1- and 3-positions. In the cyclohexyl radical, the substituents A and B are in the 2- and 6-positions, and in the cyclopentyl radical in the 2- and 5-positions.

Examples of acylphosphine oxide compounds are acylphosphine oxides and acylphosphinic acid esters. The following details may be noted with respect to formula (I):

$R^1$ may be straight-chain or branched alkyl of 1 to 6 carbon atoms, eg. methyl, ethyl, i-propyl, n-propyl, n-butyl, amyl or n-hexyl, cycloalkyl, cyclopentyl and cyclohexyl, aryl, eg. phenyl and naphthyl, halogen-substituted aryl, eg. monochlorophenyl and dichlorophenyl, alkyl-substituted aryl, eg. methylphenyl, ethylphenyl, isopropylphenyl, tert.-butylphenyl and dimethylphenyl, alkoxy-substituted aryl, eg. methoxyphenyl, ethoxyphenyl and dimethoxyphenyl, or a S-containing or N-containing five-membered or six-membered heterocyclic radical, eg. thienyl or pyridyl, $R^2$ may have one of the meanings of $R^1$ and may also be alkoxy, in particular of 1 to 6 carbon atoms, eg. methoxy, ethoxy, i-propoxy, butoxy or ethoxyethoxy, or aryloxy, eg. phenoxy, methylphenoxy, or aralkoxy, eg. benzyloxy, and $R^1$ and $R^2$ may be joined to form a ring, as, for example, in acylphosphonic acid o-phenylene esters.

$R^3$ can be, for example, cycloalkyl, phenyl or naphthyl, or a 5-membered or 6-membered heterocyclic radical, in particular containing S, N or O in the ring, eg. furyl, pyrrolyl, thienyl, pyranyl or pyridyl, which contains the substituents A and B at least in the two positions ortho to the carbonyl group. Examples of suitable substituents A and B are linear or branched alkyl, in particular of 1 to 6, preferably 1 to 4, carbon atoms, eg. methyl, ethyl, propyl, iso-propyl, butyl, iso-butyl and tert.-butyl; unsubstituted or substituted cycloalkyl, eg. cyclohexyl, unsubstituted or substituted aryl, eg. phenyl or tolyl, alkoxy and alkylthio, in particular of 1 to 6, preferably of 1 to 4, carbon atoms, eg. methoxy, ethoxy, propoxy, iso-propoxy, n-butoxy, methylthio, ethylthio, propylthio, iso-propylthio, n-butylthio, sec.-butylthio and tert.-butylthio; alkoxyalkyl, in particular of 2 to 12, preferably of 2 to 8, carbon atoms, eg. 2-methoxyethyl or tert.-butoxy-2-propyl; and halogen, especially chlorine or bromine.

The acylphosphine oxide compounds containing $R^3$ may for example be represented by the structural formulae II to VII

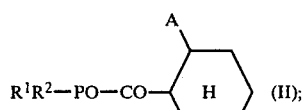 (II);
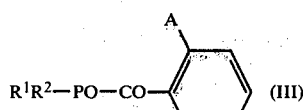 (III)
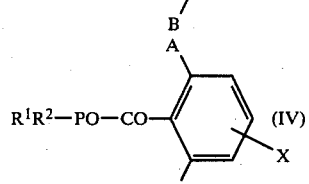 (IV)
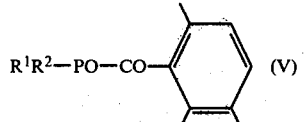 (V)
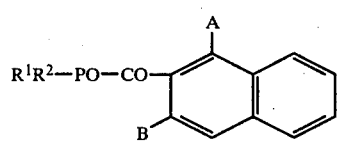 (VI)
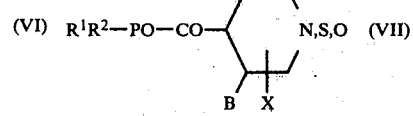 (VII)

where X represents optional additional substituents in the cycloalkyl, phenyl, naphthyl or heterocyclic radicals and has one of the meanings given for A or B.

$R^3$ can however also be tertiary alkyl or cycloalkyl (in each case with a tertiary carbon atom adjacent to the carbonyl group), eg. tert.-butyl, 1,1-dimethylheptyl, 1-methylcyclohexyl or 1-methylcyclopentyl.

The phosphine oxide compounds may be prepared by reacting an acid halide of the formula

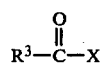

where X is Cl or Br, with a phosphine of the formula

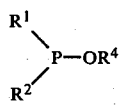

where $R^4$ is straight-chain or branched alkyl of 1 to 6 carbon atoms, or cycloalkyl of 5 or 6 carbon atoms.

The reaction can be carried out in a solvent, for example a hydrocarbon or hydrocarbon mixture, eg. petroleum ether, toluene, cyclohexane, an ether or some other conventional inert organic solvent, or even without a solvent, at from $-30°$ C. to $+130°$ C., preferably at from $10°$ to $70°$ C. The product can be directly crystallized out from the solvent, or remains after evaporation, or is distilled under reduced pressure.

The acid halide

and the substituted phosphine $R^1R^2POR^4$ are obtained by processes known to those skilled in the art from the literature (for example K. Sasse in Houben-Weyl, Volume 12/1, pages 208-209, G. Thieme-Verlag, Stuttgart).

The process for the preparation of the phosphine oxide compounds used according to the invention can for example be represented by the following equation:

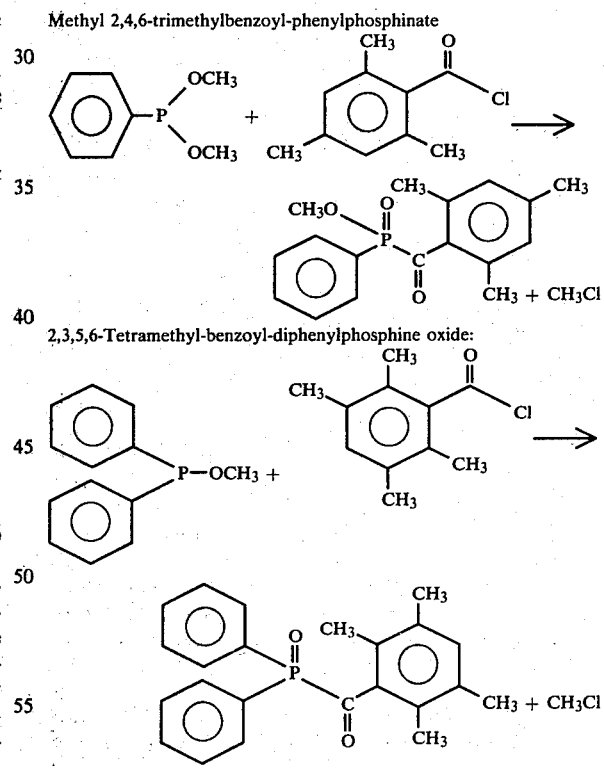

Particularly suitable recording compositions are those which contain a phosphine oxide of the formula I, where $R^1$ is aryl of 6 to 12 carbon atoms, eg. naphthyl, tolyl and especially phenyl and $R^2$ is $C_1$-$C_4$-alkoxy, eg. methoxy or ethoxy, and especially aryl of 6 to 12 carbon atoms, preferably phenyl. Photopolymerizable recording compositions containing an acylphosphine oxide compound of the formula I, where the acyl radical —CO—$R^3$ is derived from a tertiary aliphatic or cycloaliphatic carboxylic acid or from a benzoic acid which is substituted by A and B at least in the 2- and 6-positions prove to be surprisingly highly active and at the same time very stable. Very suitable acyl radicals of this type are 2,2-dimethyl-$C_4$-$C_9$-alkanoyl and 2-methyl-2-ethyl-$C_4$-$C_9$-alkanoyl radicals, and benzoyl radicals substituted by A and B, which are especially $C_1$-$C_4$-alkyl, $C_1$-$C_4$-alkoxy or halogen, in the 2- and 6-, 2-, 3- and 6-, 2-, 4- and 6- or 2-, 3-, 5- and 6-positions.

Examples of suitable phosphine oxide compounds of the formula I for use in the recording compositions according to the invention are: 2,2-dimethyl-propionyl-diphenylphosphine oxide, 2,2-dimethyl-heptanoyl-diphenylphosphine oxide, 2,2-dimethyl-octanoyl-diphenylphosphine oxide, 2,2-dimethyl-nonanoyl-diphenylphosphine oxide, methyl 2,2-dimethyl-octanoyl-phenylphosphinate, 2-methyl-2-ethyl-hexanoyl-diphenylphosphine oxide, 1-methyl-1-cyclohexanecarbonyldiphenylphosphine oxide, 2,6-dimethylbenzoyl-diphenylphosphine oxide, 2,6-dimethoxybenzoyl-diphenylphosphine oxide, 2,6-dichlorobenzoyl-diphenylphosphine oxide, methyl 2,6-dimethoxybenzoyl-phenylphosphinate, 2,4,6-trimethylbenzoyldiphenylphosphine oxide, methyl 2,4,6-trimethylbenzoyl-phenylphosphinate, 2,3,6-trimethylbenzoyl-diphenylphosphine oxide, 2,3,5,6-tetramethylbenzoyl-diphenylphosphine oxide, 2,4,6-trimethoxybenzoyl-diphenylphosphine oxide, 2,4,6-trichlorobenzoyl-diphenylphosphine oxide, 2-chloro-6-methylthio-benzoyl-diphenylphosphine oxide, methyl 2,4,6-trimethylbenzoyl-naphthylphosphinate, 1,3-dimethoxynaphthalene-2-carbonyl-diphenylphosphine oxide, 2,8-dimethoxynaphthalene-1-carbonyl-diphenylphosphine oxide, 2,4,6-trimethylpyridine-3-carbonyl-diphenylphosphine oxide, 2,4-dimethylquinoline-3-carbonyl-diphenylphosphine oxide, 2,4-dimethoxyfuran-3-carbonyl-diphenylphosphine oxide and methyl 2,4-dimethylfuran-3-carbonyl-phenylphosphinate.

The recording compositions according to the invention may contain phosphine oxide compounds of the formula I as the sole photoinitiators, in general in an amount of from 0.005 to 10, especially from 0.005 to 5, % by weight based on the total amount of the photopolymerizable recording composition, but it is also possible to use the phosphine oxide compounds in the photopolymerizable recording compositions in combination with conventional photoinitiators. Examples of the latter which are suitable are those of the ketone type, eg. benzil dimethylketal, α-hydroxyisobutyrophenone, diethoxyacetophenone, α-methylolbenzoin ethyl ether, benzoin methyl ether and benzoin isopropyl ether.

It is frequently advantageous to use the phosphine oxide compounds of the formula I in the recording compositions in combination with tertiary amines, eg. methyldiethanolamine, dimethylethanolamine, triethanolamine or ethyl p-dimethylaminobenzoate. The total concentration of initiator system (photoinitiator plus amines) is from 0.05 to 15% by weight, based on the total amount of the photopolymerizable recording composition, the proportion of amine preferably being at least half the total initiator content.

Low molecular weight compounds possessing at least one photopolymerizable olefinically unsaturated double bond which are suitable for use in the mixture of (a) and (b), which is the basis of the recording composition according to the invention, are the monomers conventionally used in such compositions, provided they form compatible mixtures with the particular polymeric binders selected and provided they boil above 100° C. under atmospheric pressure. In general, they have a molecular weight of less than 2,000 and in particular less than 1,000. It is preferred to use monomers possessing two or more olefinically unsaturated photopolymerizable double bonds, either by themselves or as mixtures with monomers possessing only one olefinically unsaturated photopolymerizable double bond, in which case the proportion of the latter monomers is in general only from about 5 to 50, preferably from 5 to 30, % by weight of the total amount of monomers. The nature of the monomers used depends largely on the nature of the polymeric binder used. For example, in the case of mixtures with unsaturated polyester resins, particularly suitable polymers are allyl compounds containing two or more double bonds, eg. diallyl maleate, allyl acrylate, diallyl phthalate, diallyl trimellitate, triallyl trimellitate and ethylene glycol bis-allyl-carbonate, and diacrylates, polyacrylates, dimethacrylates and polymethacrylates, as obtainable, for example, by esterifying diols or polyols with acrylic acid or methacrylic acid, eg. the diacrylates and dimethacrylates of ethylene glycol, diethylene glycol, triethylene glycol, polyethylene glycol of molecular weight up to about 500, propane-1,2-diol, propane-1,3-diol, neopentylglycol (2,2-dimethyl-propanediol) and butane-1,4-diol, and the triacrylates and trimethacrylates of 1,1,1-trimethylolpropane, glycerol and pentaerythritol, as well as the monoacrylates and monomethacrylates of such diols and polyols, eg. ethylene glycol monoacrylate, diethylene glycol monoacrylate, triethylene glycol monoacrylate and tetraethylene glycol monoacrylate, and monomers, containing two or more olefinically unsaturated bonds and also containing urethane groups and/or amide groups, eg. the low molecular weight compounds prepared from aliphatic diols of the above type, organic diisocyanates and hydroxyalkyl acrylates or methacrylates. Further examples of suitable compounds are acrylic acid, methacrylic acid and their derivatives, eg. acrylamide, methacrylamide, N-hydroxymethylacrylamide, N-hydroxymethylmethacrylamide and acrylates and methacrylates of monoalcohols of 1 to 6 carbon atoms. Mixtures of allyl monomers with diacrylates or polyacrylates are very suitable. If mixtures containing polyamides as polymeric binders are employed, suitable types of monomers, amongst those mentioned, are the diacrylates and polyacrylates and especially those monomers which in addition to the double bonds contain amide and/or urethane groups, such as acrylamide derivatives, eg. the reaction products of 2 moles of N-hydroxymethylacrylamide or N-hydroxymethylmethacrylamide with 1 mole of an aliphatic diol, eg. ethylene glycol, xylylene-bis-acrylamide or an alylene-bis-acrylamide, where alkylene is of 1 to 8 carbon atoms. Water-soluble monomers, eg. hydroxyethyl acrylate, hydroxyethyl methacrylate, and monoacrylates, monomethacrylates, diacrylates and dimethacrylates of polyethylene glycol having a molecular weight of from about 200 to 500 are particularly suitable for the preparation of recording compositions which can be developed in aqueous alkaline solutions, for example for the preparation of printing plates containing polyvinyl alcohol, a polyvinyl alcohol alkoxylation product or polyvinylpyrrolidone as polymeric binder. In combination with elastomeric diene polymers as the binders, for example with polystyrene-polyisoprene-polystrene three-block copolymers, polystyrene-polybutadiene two-block copolymers or polystrene-polyisoprene two-block copolymers, the polyacrylates or polymethacrylates of polyols, and especially of glycols of not less than 4 carbon atoms, have proved particularly suitable.

Suitable organic polymeric binders (b) for the mixtures constituting the photopolymerizable recording compositions, and especially for the preparation of printing plates and relief plates, are the polymers conventionally used for this purpose, which should in general be compatible with the low molecular weight compounds (a) used in the mixture and, as is evident to those skilled in the art, should be soluble or dispersible in a suitable developer solution in order to make it possible, after imagewise exposure, to wash out the unexposed and non-crosslinked areas of a layer of the photopolymerizable recording composition. Examples of suitable saturated or unsaturated binders are linear polyamides and in particular alcohol-soluble copolyamides as described in French Pat. No. 1,520,856, cellulose derivatives, especially those which can be washed out with aqueous alkaline solutions, vinyl alcohol polymers, polymers and copolymers of vinyl esters of aliphatic monocarboxylic acids of 1 to 4 carbon atoms, eg. vinyl acetate, hydrolyzed to various degrees, polyurethanes, polyether-urethanes, polyester-urethanes, and unsaturated polyester resins, as described, for example, in German Laid-Open Application DOS No. 2,040,390. Amongst the linear or branched polyesters obtained by reacting unsaturated dibasic carboxylic acids, with or without unsaturated polybasic carboxylic acids and with or without saturated dibasic and polybasic carboxylic acids, with dialcohols, which may also contain polyalcohols, those having a relatively high acid number, in particular an acid number from 75 to 160, are preferred, since they result in recording compositions which exhibit good dispersibility or solubility in aqueous alkaline developer solutions. Regarding the composition and preparation of unsaturated polyester resins, references may be made to the existing literature, for example to the book by H. V. Boenig, Unsaturated Polyesters, Structure and Properties, Amsterdam 1964.

The recording compositions according to the invention consist in the main, ie. to the extent of more than 50% by weight, and preferably of from 70 to 100% by weight, of the photoinitiator-containing mixture of (a) and (b). The content of polymeric binder (b) in this mixture is in general from about 45 to 90, and in particular from 45 to 65, % by weight, based on the sum of the amount of polymer (b) and photopolymerizable low molecular weight compound (a).

It is often advantageous to add to the photopolymerizable compositions the conventional amounts of known thermal polymerization inhibitors, for example hydroquinone, p-methoxyphenol, p-dinitrobenzene, p-quinone, methylene blue, β-naphthol, N-nitrosamines, eg. N-nitrosodiphenylamine, phenothiazine, esters of phosphorous acid, eg. triphenyl phosphite, or salts, especially alkali metal salts and aluminum salts, of N-nitroso-cyclohexyl-hydroxylamine.

The compounds can also contain other conventional additives, for example plasticizers, saturated low molecular weight compounds containing amide groups, waxes and the like.

The photopolymerizable recording compositions can be processed by conventional methods into, for example, photopolymer printing plates having the recording composition as the relief-forming layer. The precise method depends on the nature of the mixture of (a)+(b) and on whether the composition is fluid or solid.

The recording compositions are processed into, for example, relief plates in the conventional manner, by imagewise exposure to actinic light, using light sources which have emission maxima in the absorption range of the photoinitiator, in general in the range from 200 to 500 nm and particularly from 230 to 450 nm, or which emit light of which a sufficient proportion is within this wavelength range, such as actinic or superactinic fluorescent tubes, low-pressure, medium-pressure and high-pressure mercury vapor lamps, which may or may not be doped, and xenon lamps.

After imagewise exposure, the unexposed areas of the layer of recording composition are removed in the conventional manner, either mechanically or by washing out with a suitable developer solution, and the resulting plate, for example a relief printing plate, is dried. In some cases, it may be advantageous to after-expose the entire relief.

The photopolymerizable recording compositions according to the invention are distinguished by high reactivity on exposure, thus enabling the exposed areas of the layer to cure more rapidly. It is surprising that the recording compositions nevertheless exhibit excellent shelf life. It is a particular advantage of the novel photopolymerizable recording compositions that it is frequently possible to dispense with pre-exposure before imagewise exposure of the layer, and nevertheless to employ short exposure times. A further unexpected major advantage is that layers of the recording compositions according to the invention, as shown in Example 10, when processed into relief printing plates, gives improved relief images, thereby resulting, for example, in substantially improved reverse prints.

In the Synthesis Examples, Examples and Comparative Experiments, parts and percentages are by weight, unless stated otherwise. Parts bear the same relation to parts by volume as the kilogram to the liter. Synthesis Examples of acylphosphine oxide compounds of the formula I:

SYNTHESIS EXAMPLE S 1

2,4,6-Trimethylbenzoyl-diphenylphosphine oxide 225 parts of diphenylchlorophosphine, dissolved in 220 parts by volume of petroleum ether, are added to a mixture of 1,350 parts by volume of petroleum ether (boiling range 40°–70° C.), 180 parts by volume of N,N-diethylaniline and 67 parts by volume of methanol at 0° C., whilst stirring. The mixture is then stirred for 2 hours at room temperature. After cooling the mixture to about +5° C., the amine hydrochloride which has separated out is filtered off and the filtrate is initially distilled at 10–20 mm Hg in order to remove all volatiles. The diphenylmethoxyphosphine is then subjected to fractional distillation at 0.1–1 mm Hg. Boiling point 120°–124° C./0.5 mm Hg. Yield, 175 parts (80%, based on diphenylchlorophosphine).

648 parts of methoxydiphenylphosphine are added slowly to 547.5 parts of 2,4,6-trimethylbenzoyl chloride at 50°–95° C. in a stirred apparatus equipped with a reflux condenser and dropping funnel. The mixture is then stirred for 4–5 hours at 50° C., the contents of the flask are dissolved in ether at 30° C., and petroleum ether is added until the mixture starts to turn cloudy. On cooling, 910 parts (87% of theory) of 2,4,6-trimethylbenzoyl-diphenylphosphine oxide crystallize. Pale yellow crystals, melting point 89°–92° C.

Analysis: C calculated 75.86, H calculated 6.03, P calculated 8.91. C found 75.9, H found 6.1, P found 8.9.

SYNTHESIS EXAMPLE S 2

2,6-Dimethoxybenzoyl-diphenylphosphine oxide

Following the method described in Example S 1, 20 parts of 2,5-dimethoxybenzoyl chloride are suspended in 20 parts by volume of toluene and 21.6 parts of methoxydiphenylphosphine are added dropwise to this mixture at 50°-55° C., whilst stirring. The mixture is then stirred for 3 hours at 50° C., after which the product is directly recrystallized from toluene. 32 parts (88% of theory) of 2,6-dimethoxybenzoyl-diphenylphosphine oxide are obtained. Yellowish crystals, melting point 124°-126° C.

Analysis: C calculated 68.85, H calculated 5.19, P calculated 8.47. C found 68.7, H found 5.4, P found 8.2.

SYNTHESIS EXAMPLE S 3

2,2-Dimethyloctanecarbonyl-diphenylphosphine oxide (Versatoyl-diphenylphosphine oxide)

Following the method described in Example S 1, 43.2 parts of methoxydiphenylphosphine are added dropwise to 38.3 parts of 2,2-dimethyl-heptanecarboxylic acid chloride (Versatic acid chloride) at 50° C. The mixture is stirred for 3 hours at 50° C., then cooled to 15° C., and stirred into a slurry of 60 parts of silica gel in 350 parts by volume of toluene. The batch is then stirred for one hour whilst cooling with ice. It is then filtered and the solvent is distilled from the filtrate under reduced pressure. Versatoyl-diphenylphosphine oxide remains as a viscous oil. Yield 64.5 parts (90% of theory).

Analysis: C calculated 74.16, H calculated 8.15, P calculated 8.71. C found 74.3, H found 8.4, P found 8.5.

EXAMPLE 1

A 65% strength solution in methanol of a mixture comprising 60% of a copolyamide of adipic acid, hexamethylenediamine, 4,4'-diaminodicyclohexylmethane and ε-caprolactam, 25% of the diether of 1 mole of ethylene glycol with 2 moles of N-hydroxymethyl acrylamide, 13.2% of benzenesulfonamide and 1.8% of 2,4,6-trimethylbenzoyl-diphenylphosphine oxide, also containing 0.2% of the aluminum salt of N-nitrosocyclohexylhydroxylamine and 0.01% of a black dye (Color Index No. 12,195) is prepared. A layer of the solution is cast onto a steel sheet provided with a layer of adhesive, the amount of solution being such that after drying at about 70° C. a 680 μm thick layer of the photopolymerizable recording composition is obtained. Following the procedure described in the text preceding the Examples, the photopolymer printing plate obtained is exposed imagewise through an imagebearing transparency, and the unexposed areas of the layer are then washed out with an alcohol-water mixture. For satisfactory reproduction of a 3% highlight dot (60 lines/cm screen, the plate requires a minimum exposure time of 4 minutes when using superactinic fluorescent tubes at a distance of 5 cm.

EXAMPLE 2

The procedure followed is as described in Example 1, except that only 11.4% of benzenesulfonamide are employed, but 1.8% of methyldiethanolamine are also added. The minimum exposure time is only 3 minutes.

EXAMPLE 3

The procedure described in Example 1 is followed, except that 1.8% of 2,6-dimethoxybenzoyldiphenylphosphine oxide are used as the phosphine oxide photoinitiator. The minimum exposure time is 4.5 minutes.

EXAMPLE 4

The procedure described in Example 2 is followed, except that 1.8% of 2,6-dimethoxybenzoyldiphenylphosphine oxide are used as the initiator. The minimum exposure time is only 2.5 minutes.

EXAMPLE 5

The procedure described in Example 2 is followed, except that 1.8% of Versatoyl-diphenylphosphine oxide (2,2-dimethyloctanecarbonyldiphenylphosphine oxide) are used as the initiator. The minimum exposure time is 3.5 minutes.

COMPARATIVE EXPERIMENT A

The procedure followed is as described in Example 1, except that 1.8% of benzil dimethylketal are used as the photoinitiator. Under otherwise comparable conditions, the minimum exposure time is 5 minutes. Accordingly, the reactivity of the recording compositions according to the invention is from 25 to 100% higher.

EXAMPLE 6

The procedure described in Example 1 is followed. However, no dye is added and instead of the aluminum salt, the potassium salt of N-nitrosocyclohexylhydroxylamine is used. The layer of the photopolymerizable recording composition is 500 μm thick when dry. For satisfactory reproduction of a 3% highlight dot (34 lines/cm screen), as is, for example, frequently used in newspaper printing, a minimum exposure time of 50 seconds is required if the exposure is carried out with a commercial iron-modified high-pressure mercury lamp with reflector, at a distance of 50 cm, the UV lamp having a power consumption of 3,000 watt/hour. Further processing of the plate is carried out as described in Example 1.

EXAMPLE 7

The procedure described in Example 6 is followed, except that only 11.4% of benzenensulfonamide are used and the composition additionally contains 1.8% of methyldiethanolamine. The minimum exposure time is only 35 seconds.

EXAMPLE 8

The procedure described in Example 6 is followed, except that only 11.4% of benzenesulfonamide are used and 0.9% of methyldiethanolamine and 0.9% of benzil dimethylketal is also added. Furthermore, instead of 2,4,6-trimethylbenzoyldiphenylphosphine oxide 1.8% of 2,6-dimethoxybenzoyldiphenylphosphine oxide are used. The minimum exposure time is here again 35 seconds.

COMPARATIVE EXPERIMENT B

The procedure described in Example 6 is followed, except that 1.8% of benzil dimethylketal are used as the photoinitiator. The minimum exposure time under the stated conditions is 55 seconds.

EXAMPLE 9

400 parts of a mixture of equal amounts of tetraethylene glycol dimethacrylate and diallyl phthalate, 2 parts of hydroquinone and 7 parts of 2,4,6-trimethylbenzoyl-diphenylphosphine oxide are added to 650 parts of an unsaturated polyester, obtained from fumaric acid, trimellitic anhydride and diethylene glycol and having an acid number of 140. 110 ppm of N-nitrosidiphenylamine are added to the resulting liquid recording composition.

Relief printing plates are produced from the recording composition in the conventional manner. For this purpose, the liquid recording composition is cast onto a sheet steel support provided with a layer of adhesive, the thickness of the recording layer is brought to 800 μm with a knife coater, and the layer is then covered with a 6 μm thick transparent polyester film, while avoiding the inclusion of air. The fluid layer of the recording composition is exposed imagewise through a negative, placed on the polyester film, using a commercial medium-pressure mercury vapor lamp. The negative and polyester film are removed and the unexposed areas of the layer of recording composition are then washed out with an 0.5% strength aqueous sodium carbonate solution. The resulting relief plate is dried and at the same time subjected to post-exposure of 2 minutes. The correct exposure time, at which all the required elements of the relief, ie. 3% highlight dots (40 lines/cm screen), isolated dots of 0.3 mm diameter, and fine lines having a width of 0.7 mm, are satisfactorily anchored to the metal support, is found to be 9 exposure units, as measured with a commercial automatic exposure meter, under the particular conditions described. The printing relief obtained is satisfactory and meets the requirements placed thereon.

COMPARATIVE EXPERIMENT C

The procedure followed is exactly as described in Example 9 except that instead of the 2,4,6-trimethylbenzoyldiphenylphosphine oxide 8 parts of benzil dimethylketal are used.

Using this liquid recording composition, the requisite exposure time is found, by the method described above, to be 23 exposure units, ie. 2.5 times longer.

EXAMPLE 10

294 parts of a partially hydrolyzed polyvinyl acetate (degree of hydrolysis 82 mole %, mean molecular weight 500) are dissolved in 294 parts of water by stirring for several hours at 90° C. After cooling the solution to 70° C., 200 parts of a monomer mixture prepared from 180 parts of 2-hydroxyethyl methacrylate, 20 parts of 1,1,1-trimethylolpropane triacrylate, 10 parts of 2,4,6-trimethylbenzoyldiphenylphosphine oxide and 2 parts of 2,6-di-tert.-butyl-p-cresol are added whilst stirring.

The homogeneous, viscous solution is filtered and degassed under reduced pressure. It is then applied to a steel sheet provided with a layer of adhesive and dried for 24 hours at room temperature, to give a 500 μm thick non-tacky layer of the recording composition. After a pre-exposure of 2 seconds, followed by an exposure of 40 seconds through a negative in a flat-plate unit employing fluorescent tubes, washout with water in a spray washer and drying at 100° C., a plate is obtained which exhibits a good relief image and excellent mechanical properties and which gives several thousand prints. In a printing test, the relief printing plate gives well-defined legible reverse prints which fully meet newspaper printing requirements.

EXAMPLE 11

A printing plate is prepared by the method described in Example 10, except that the recording composition contains, instead of 2,4,6-trimethylbenzoyl-diphenylphosphine oxide, an equal amount of 2,6-dimethoxybenzoyl-diphenylphosphine oxide. The pre-exposure time is about 2 seconds and the time required for imagewise exposure is 45 seconds.

COMPARATIVE EXPERIMENTS D and E

A printing plate is prepared by the method described in Example 10, except that the recording composition contains, as the photoinitiator, the same amount of the conventional initiators benzil dimethylketal (Comparative Experiment D) and benzoin isopropyl ether (Comparative Experiment E) in place of the phosphine oxide. Comparison of the required exposure time of the recording compositions, each of which contains the same amount of photoinitiator, gives the following results:

| Recording composition containing | Pre-exposure | Imagewise exposure |
|---|---|---|
| 2,4,6-Trimethylbenzoyldiphenyl-phosphine oxide (Example 10) | 2 seconds | 40 seconds |
| 2,6-Dimethoxybenzoyldiphenylphosphine oxide (Example 11) | 2 seconds | 45 seconds |
| Benzil dimethylketal (Comparative Experiment D) | 4 seconds | 90 seconds |
| Benzoin isopropyl ether (Comparative Experiment E) | 6 seconds | 120 seconds |

Relief printing plates prepared with the recording composition of Comparative Experiment D give, in a printing test, less well defined and less sharp reverse prints than those obtained with the relief printing plate prepared according to Example 10.

EXAMPLE 12 AND COMPARATIVE EXPERIMENT F

Separate printing plates are prepared in the same way as in Example 10, with the sole difference that the photopolymerizable layer of the recording composition contains, in one case, 2,4,6-trimethylbenzoyldiphenylphosphine oxide (Example 12) and in the other case benzil dimethylketal (Comparative Experiment F). The various plates, without being pre-exposed, are exposed imagewise through a negative, using a commercial iron-doped high-pressure mercury vapor lamp with reflector, at a distance of 75 cm, the power consumption of the UV lamp being 5 kW/hour; the required minimum exposure time is determined. It is 60 seconds in the case of the printing plates of Example 12 (according to the invention) and 110 seconds in the case of those of Comparative Experiment F.

We claim:

1. A photopolymerizable recording composition for the preparation of printing plates and relief plates, which consists mainly of a mixture, containing (a) a photoinitiator, (b) one or more monomers possessing one or more photopolymerizable olefinically unsaturated double bonds and (c) one or more organic polymeric binders, the improvement wherein the photoinitiator is an acylphosphine oxide compound of the formula

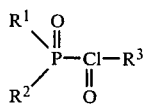

(I)

where
- $R^1$ is alkyl of 1 to 6 carbon atoms, cycloalkyl of 5 or 6 ring carbon atoms, aryl which is unsubstituted or substituted by halogen, alkyl or alkoxy, or an S-containing or N-containing five-membered or six-membered heterocyclic radical,
- $R^2$ has the same meanings as $R^1$, or is alkoxy, aryloxy or aralkoxy, $R^1$ and $R^2$ being the same or different or together form a ring, and
- $R^3$ is tertiary alkyl of 4 to 18 carbon atoms or tertiary cycloalkyl of 5 or 6 ring carbon atoms or is a cycloalkyl, aryl or 5-membered or 6-membered heterocyclic radical containing S, N or O as hetero atoms which contains substituents A and B bonded at least to the two ring carbon atoms, capable of substitution, which are adjacent to the point of attachment of the carbonyl group to the carbonyl group, A and B being identical or different and each being alkyl, alkoxy, alkoxyalkyl, alkylthio, cycloalkyl, aryl or halogen.

2. The photopolymerizable recording composition of claim 1, where $R^1$ is aryl of 6 to 12 carbon atoms and $R^2$ is alkoxy of 1 to 4 carbon atoms or aryl of 6 to 12 carbon atoms.

3. The photopolymerizable recording composition of claim 1, where $R^3$ is tertiary alkyl of 4 to 18 carbon atoms or tertiary cycloalkyl of 5 or 6 ring carbon atoms.

4. The photopolymerizable recording composition of claim 1, which contains an acyl phosphine oxide compound of the formula (I), where $R^3$ is phenyl substituted by groups A and B at least in the 2- and 6-positions.

5. The photopolymerizable recording composition of claim 1, which additionally contains a tertiary amine, the amount of amine making up at least half of the total initiator content.

6. The photopolymerizable recording composition of claim 1, wherein the organic polymeric binder is a linear polyamide, an unsaturated polyester or a polymer with recurring vinyl alcohol groups in the main chain of the molecule.

* * * * *